Figure 1:
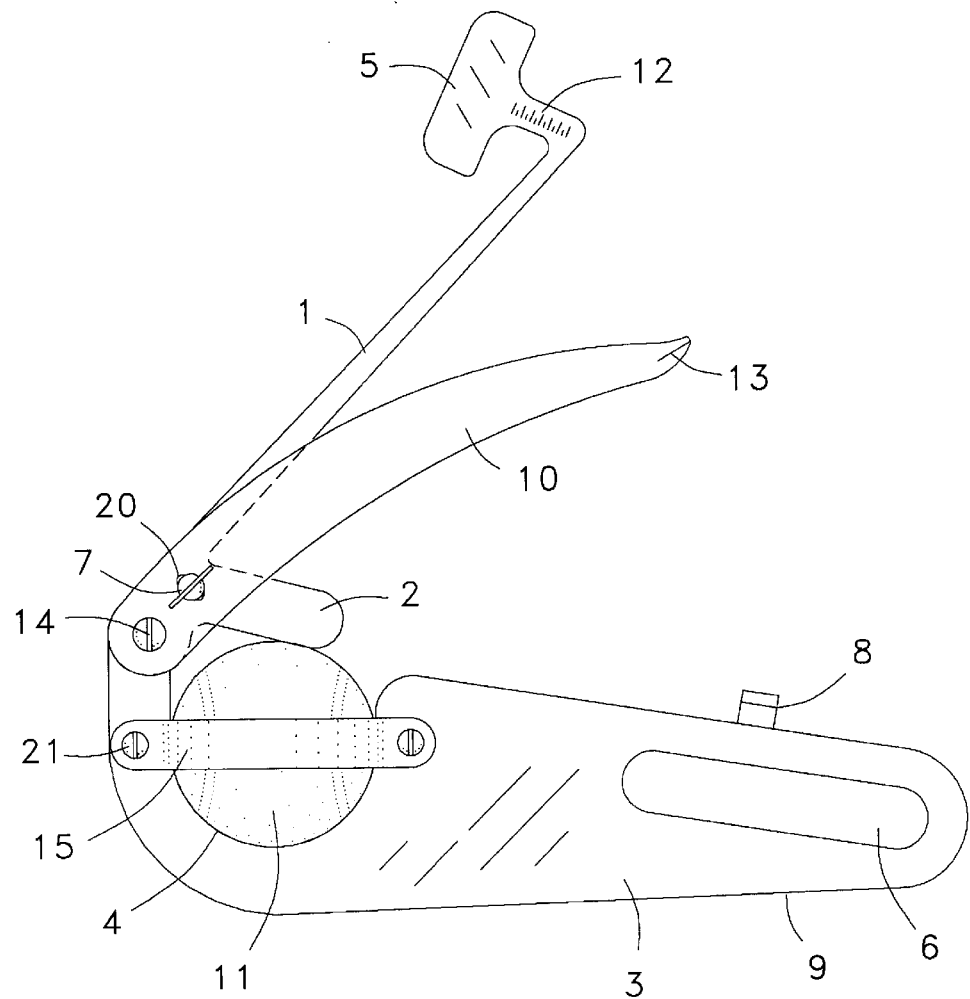

United States Patent
Slenker

[11] Patent Number: 5,837,889
[45] Date of Patent: Nov. 17, 1998

[54] PRESSURE GAUGE FOR PNEUMATIC BALLS

[76] Inventor: Stephen Amram Slenker, 10 Crabapple Ln., Chelmsford, Mass. 01824

[21] Appl. No.: 798,877

[22] Filed: Feb. 11, 1997

[51] Int. Cl.⁶ .............. G01N 3/42; G01N 3/48; G01N 3/68
[52] U.S. Cl. ................. 73/81; 73/818; 73/860
[58] Field of Search .................. 73/81, 82, 818, 73/1.89, 1.57, 860, 85

[56] References Cited

U.S. PATENT DOCUMENTS

| | | | |
|---|---|---|---|
| 1,376,413 | 5/1921 | Fairholme et al. | 73/81 |
| 1,771,858 | 7/1930 | Mohr | 73/81 |
| 2,278,416 | 4/1942 | Atti | 73/818 |
| 2,626,522 | 1/1953 | Brown | 73/818 |
| 2,628,496 | 2/1953 | Wick | 73/818 |
| 3,138,951 | 6/1964 | Scott | 73/81 |
| 3,376,734 | 4/1968 | Ether | 73/78 |
| 4,136,554 | 1/1979 | Larson | 73/81 |
| 4,590,808 | 5/1986 | Lightfoot et al. | 73/818 X |
| 5,222,391 | 6/1993 | Reenstra | 73/81 |
| 5,291,774 | 3/1994 | Putnam | 73/82 |
| 5,511,410 | 4/1996 | Sherts | 73/81 |
| 5,567,870 | 10/1996 | Harris | 73/81 |
| 5,639,969 | 6/1997 | D'Adamo | 71/81 X |

FOREIGN PATENT DOCUMENTS

| | | | |
|---|---|---|---|
| 826073 | 11/1951 | Germany | 73/82 |
| 1264101 | 2/1968 | Germany | 73/81 |
| 7601334 | 8/1977 | Netherlands | 73/81 |
| 198774 | 6/1967 | U.S.S.R. | 73/81 |
| 204651 | 10/1967 | U.S.S.R. | 73/81 |
| 479098 | of 1938 | United Kingdom | 73/760 |

OTHER PUBLICATIONS

Patent Abstracts of Europe "Test device for a tennis ball" (DE 03627359A1) Feb. 18, 1988 Ingo Kern et al.

Patent Abstracts of Japan "Measuring Method for Internal Pressure of Tennis Ball" (O6–229864) Aug. 19, 1994 Yoshiyuki Hirocke et al.

Primary Examiner—Thomas P. Noland
Attorney, Agent, or Firm—John V. Stewart

[57] ABSTRACT

A pressure gauge for tennis balls and the like, comprising a rigid clamp arm pivotally connected to a flexible clamp arm for squeezing a ball between them. The rigid clamp arm has a socket for holding the ball. The flexible clamp arm preferably has a probe which extends into the socket and depresses the ball when said two clamp arms are rotated toward each other in a clamping action. A pointer arm is journalled to the fulcrum of the clamp arms and is attached to the flexible clamp arm near the fulcrum with a screw, which can be loosened for calibration. A scale adjacent the free end of the pointer indicates the pointer displacement when the two clamp arms are pivoted together. The pointer provides high sensitivity to distinguish small differences in ball pressure.

10 Claims, 3 Drawing Sheets

PRESSURE GAUGE FOR PNEUMATIC BALLS

BACKGROUND

1. Field

This invention relates to devices for testing the pressure of pneumatic balls, such as tennis balls, especially hand-held, manually operated devices.

2. Prior art

Most tennis players have a number of used tennis balls in their bags of questionable condition. When tennis balls degrade, they lose some of their pressure. It is difficult to determine the condition of a tennis ball except by playing with it. Testing by bouncing, dropping, or squeezing is inaccurate, since the difference in pressure between a good and bad ball is typically less than 5 percent. If a ball is squeezed between the fingers and thumb with 178N (40 pounds) of thumb force, the difference between a good and bad ball is less than 1.5 mm (1/16 inch) of separation between the fingers and thumb. There is no accurate way to measure this indentation, and the related condition of the ball, unless a gauge is used.

The prior art discloses several tennis ball pressure gauge devices. However, these are relatively expensive and bulky, and therefore are impractical for most tennis players. For example, U.S. Pat. No. 5,291,774 (Putnam Jr.) discloses a gauge which uses a pivoting weighted arm to press downward on a ball. A scale is adjacent the free end of the arm. This device is bulky, due to the weight. Its shallow ball compression makes it less reliable for detecting small differences in pressure than the present invention. Shallow compression results in measurement of factors other than internal pressure, such as felt depth and condition, and placement of the seam.

U.S. Pat. No. 5,222,391 (Reenstra) discloses a gauge which clamps a tennis ball against an electronic force sensor. However, it requires electronic components and a battery or other power supply, cannot be calibrated by the user, and uses flat compression surfaces, which allows extraneous variability in the measurement.

U.S. Pat. No. 4,136,553 (Larson) discloses a gauge using a probe connected to a compression spring and an indicator. The user must continuously push the probe down on the ball while simultaneously reading the indicator. A locking clamp should be added to this device for easier and more reliable reading, but it already has more parts than the present invention. It is not easy with Larson's design to push a probe deep into a ball for reliable readings, as it is using the leverage of the present invention.

SUMMARY

The objective is a tennis ball pressure gauge that is small, light weight, and inexpensive, yet accurate and sensitive enough to indicate the playable condition of tennis balls, and is quick and easy to operate by the average tennis player.

These objectives are met in the invention disclosed herein. It comprises a rigid clamp arm pivotally connected to a flexible clamp arm for squeezing a ball between them. The rigid clamp arm has a socket for holding the ball. The flexible clamp arm preferably has a probe which extends into the socket and depresses the ball when the two arms are rotated toward each other in a clamping action. A pointer arm is journalled to the fulcrum of the clamp arms and is attached to the flexible clamp arm near the fulcrum with a wing screw, which can be loosened for calibration. A scale adjacent the free end of the pointer indicates the pointer displacement when the two arms are pivoted together. The pointer provides high sensitivity to distinguish small differences in ball pressure.

This device is preferably made of plastic, and is therefore lightweight. It has only a small number of parts, and they can all be molded without subsequent machining or other processes, for inexpensive manufacture. Its use is easy and fast, taking only a few seconds to test a ball. It is sensitive enough to detect differences among new balls. It is useful for measuring any type of pressurized ball, such as racquet balls, and other inflated items.

DRAWINGS

FIG. 1 Front view of gauge in open position, with ball in socket

Figure 2:
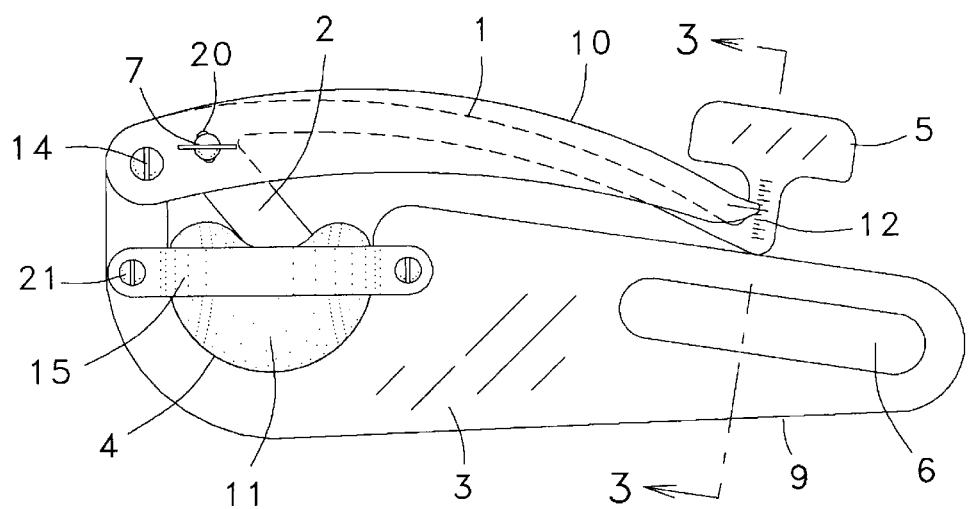

FIG. 2 Front view of gauge in testing position

Figure 3:
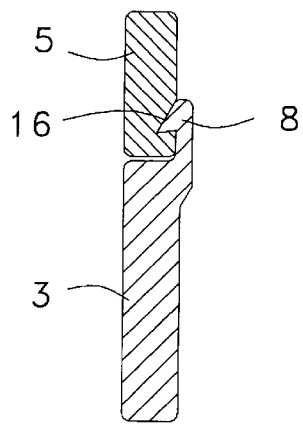

FIG. 3 Side sectional view through catch, along line 3—3 of FIG. 2

Figure 4:
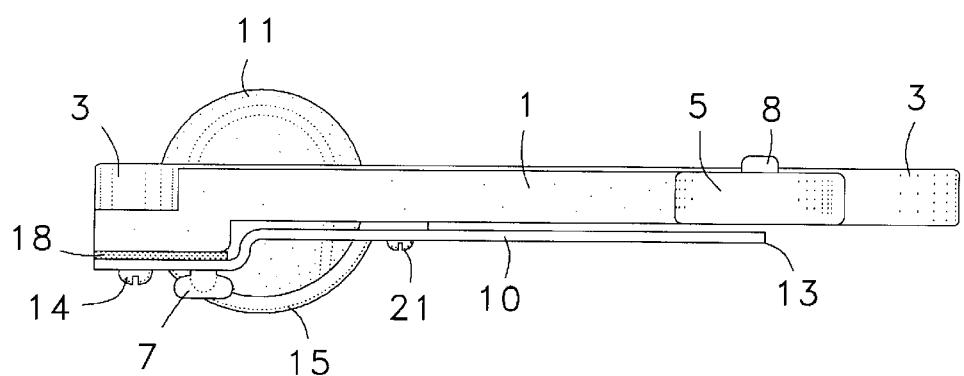

FIG. 4 Top view of gauge in testing position

Figure 5:
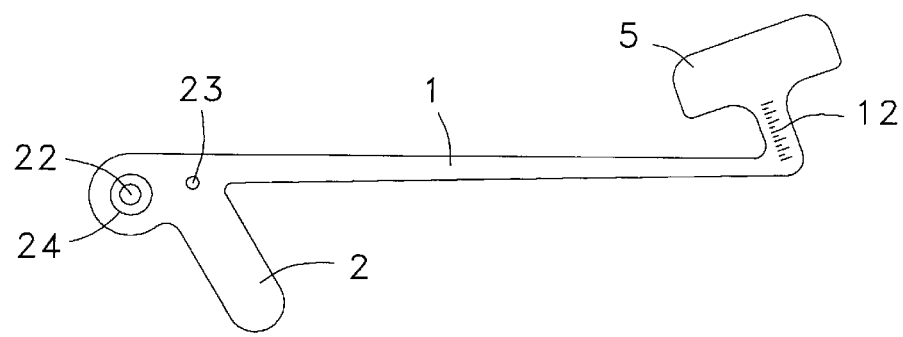

FIG. 5 Front view of flexible clamp arm

Figure 6:
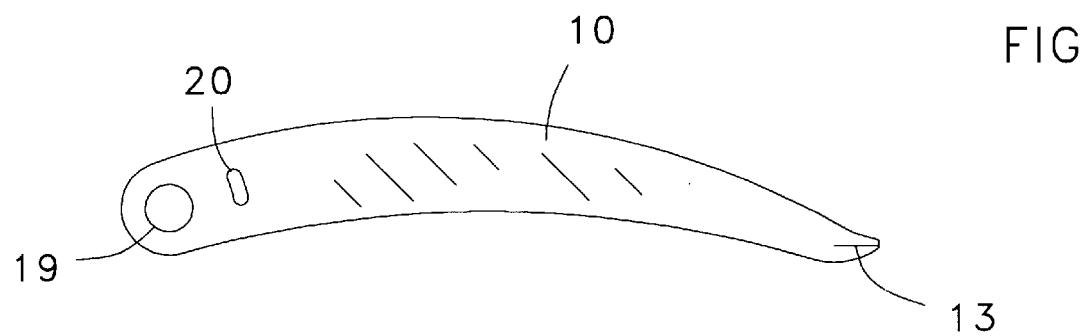

FIG. 6 Front view of pointer arm

Figure 7:
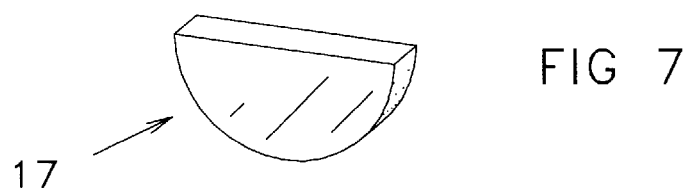

FIG. 7 Perspective view of solid insert for calibration

REFERENCE NUMERALS

1. Flexible clamp arm
2. Probe
3. Rigid clamp arm
4. Socket for holding a ball to be tested
5. Palm grip or handle of flexible clamp arm
6. Finger slot or handle of rigid clamp arm
7. Wing screw for adjusting and locking the pointer
8. Hook on rigid clamp arm
9. Lower edge of rigid clamp arm (3)
10. Pointer
11. Tennis ball
12. Scale
13. Pointer line
14. Fulcrum screw
15. Semi-circular wing
16. Hook on flexible clamp arm
17. Solid insert for calibration
18. Friction pad
19. Fulcrum journal hole in pointer
20. Adjustment slot in pointer
21. Mounting screw for semi-circular wing
22. Fulcrum screw hole
23. Attachment hole for adjustment screw
24. Washer, or short shaft on flexible clamp arm, for journal of pointer arm.

DESCRIPTION

A rigid clamp arm (3) has a socket (4) to hold a tennis ball (11), as shown in FIG. 1. A flexible clamp arm (1) is joined to the rigid clamp arm by a fulcrum screw (14). A probe (2) on the flexible clamp arm presses against the tennis ball in the socket. The ball is squeezed by the probe when two clamp arms are rotated toward each other in a clamping action. A pointer arm (10) is journalled at the fulcrum of the clamp arms, and is attached to the flexible clamp arm by a wing screw (7). The pointer arm has a line (13) which indicates the ball pressure against a scale (12). Clamping of the flexible clamp arm toward the rigid clamp arm can be done with one hand, by supporting the lower edge (9) of the rigid clamp arm (3) against the user's body, and pressing the palm grip (5) toward the user's body. An alternate closing method uses two hands, with one hand on the palm grip (5), and the other hand on the rigid clamp arm (3).

A tennis ball (11) is shown clamped in the device in FIG. 2. A ball is inserted into the socket (4). A semi-circular wing (15) on the rigid clamp arm (3) positions the ball in the socket consistently so repeatable measurements can be obtained. The flexible clamp arm (1) deflects when the probe (2) is pressed into the ball. The flexible clamp arm (1) includes a scale (12) for measurement of the ball quality. When a ball is compressed by the probe, the flexible clamp arm is flexed, but the pointer remains rigid and undistorted. The pointer position relative to the scale (12) indicates the amount of deflection of the flexible clamp arm. Initial calibration can be done by inserting a new ball, clamping the arms together, and securing them together with the latching means (8, 16). Then the pointer (10) is adjusted by loosening the wing screw (7) and setting the pointer line (13) to "0" on the scale. The quality of used balls can then be compared to the reading of the new ball.

When the flexible clamp arm is closed, it takes the shape of an arc of a circle, due to its tapered design and inherent resiliency. As seen from FIGS. 1 and 2 the arc of deflection is at least 25 degrees. This yields maximum deflection and sensitivity without exceeding the elastic limit of the material. The flexible clamp arm is preferably made of Nylon, which does not take a permanent set under normal operating conditions and use, giving repeatable readings. Means for latching the two arms together in the clamped position is provided. This is shown in FIG. 3 as a hook (8) on the rigid clamp arm, and an interlocking hook (16) on the flexible clamp arm. This latching means permits the rotational forces applied by the palm of the hand on rest (5) to be removed, and substantially increases the accuracy of the device. Any type of latching mechanism can be used.

A semicircular solid insert (17) as in FIG. 7, can be used to calibrate the device by placing the insert in the ball socket (4) of the rigid clamp arm (3), and closing and latching the flexible clamp arm. Then the pointer (10) is adjusted by loosening the wing screw (7) and setting the calibration line on the pointer to "0" on the scale (12). The solid insert should be releasably attached to a side of the rigid clamp arm (3) for convenient storage.

A friction pad (18), such as piece of cork, is placed between the pointer and the flexible clamping arm. This provides friction between these elements, and permits the pointer to maintain position, even if the wing screw is not fully tightened. This feature permits instant re-calibration, and is used for rapid comparison between balls, to obtain a matched set.

The preferred embodiment is shown in all the figures herein. However, alternate forms of this invention are possible. For example, the latching mechanism can be of any simple type. The pointer can be attached to either end of the flexible clamp arm, with the scale attached to the opposite end of the flexible clamp arm, or nearby on the rigid clamp arm. The pointer can be molded as part of the flexible clamp arm, permanently attached to either end thereof, and the scale can be attached to the other end of the flexible clamp arm, or nearby on the rigid clamp arm, by a screw that provides height adjustment of the scale for calibration. The probe is optional, although it reduces irrelevant variability in the measurement. The probe can be attached to the rigid arm, and the socket can be formed in the flexible arm. These are examples of modifications which conform to the scope and spirit of the present invention.

To operate the preferred embodiment, a tennis ball is placed in the socket (4) against the semi-circular wing (15). The handle (5) of the flexible clamp arm (1) is pushed toward the fixed arm (3) until the hooks (8, 16) on the clamp arms interlock. Manual pressure is then removed from the handle (5), and the pointer position on the scale (12) is read. This operation only takes seconds.

To calibrate the pointer, the same operation as above is done with a new ball, a comparison ball, or a solid insert (17) provided with the device. With the ball or solid insert in place, and the arms latched together, the wing screw is loosened, and the pointer is moved a desired position, such the known standard ball pressure, or zero, on the scale. Then the wing screw is tightened.

If the frictional pointer fixing feature is present, the wing screw (7) may remain loose after the calibration step above, and for immediately subsequent testing steps to find a matched set of balls. This allows temporary calibration to a non-standard ball, such as a used ball in a number of used balls to be compared for matched pressure.

SCOPE

Although the present invention has been described and shown herein with respect to a preferred embodiment, it will be understood that the foregoing description is intended to be illustrative, not restrictive. Many modifications of the present invention will occur to those skilled in the art. All such modifications which fall within the scope of the appended claims are intended to be within the scope and spirit of the present invention.

I claim:

1. A pressure gauge for pneumatic balls, comprising a rigid clamp arm, a flexible clamp arm pivotally connected to said rigid clamp arm at a mutual fulcrum, the two clamp arms capable of compressing a ball between them, and scale means for indicating the amount of deflection in said flexible clamp arm caused by the ball compression, whereby an indication of gas pressure in a pneumatic ball is obtained by placing the ball between the two clamp arms, compressing the ball by pivoting the two arms toward each other, and observing the amount of deflection in said flexible clamp arm as shown by said scale means.

2. The pressure gauge of claim 1, wherein said flexible clamp arm is designed for deflection of at least 25 degrees between a non-stressed and a stressed state.

3. The pressure gauge of claim 1, wherein said flexible clamp arm is designed to flex into a circular arc of at least 25 degrees included angle.

4. A pressure gauge for pneumatic balls, comprising:

a rigid clamp arm having first and second ends;

a flexible clamp arm having first and second ends;

the first end of said flexible clamp arm pivotally connected to the first end of said rigid clamp arm;

a ball holding socket in an intermediate portion of said rigid clamp arm facing said flexible clamp arm;

a pressure point on an intermediate portion of said flexible clamp arm for partially compressing a ball in the socket when the two clamp arms are pivoted toward each other;

a pointer arm having first and second ends;

the first end of said pointer arm connected to the first end of said flexible clamp arm;

a measurement scale attached to the second end of said flexible clamp arm for indicating the position of the second end of said pointer arm relative to the second end of said flexible clamp arm;

whereby a ball can be placed in the socket, and the two clamp arms pivoted toward each other, partially compressing the ball, and flexing the flexible arm in an amount indicated by the position of the second end of said pointer arm on the scale.

5. The pressure gauge of claim 4, wherein the first end of said pointer arm is pivotally connected to the first end of said flexible clamp arm, and further comprising a second connection between said pointer arm and said flexible clamp arm, said second connection having fastener means for adjusting the angle of said pointer arm relative to said flexible clamp arm, whereby the position of the second end of said pointer arm relative to said measurement scale is adjustable for calibration.

6. The pressure gauge of claim 5, further comprising a semi-circular solid block for insertion in said ball holding socket to provide a standard solid contact point for said pressure point on the flexible arm for calibration adjustment of said pointer arm.

7. The pressure gauge of claim 4, wherein said pressure point on the flexible arm comprises a probe protruding partially into said ball holding socket.

8. The pressure gauge of claim 4, further comprising means for releasably latching the second end of said rigid clamp arm to the second end of said flexible clamp arm; whereby pressure measurement of the ball being tested can be made under consistent, repeatable force conditions on the flexible arm.

9. A pressure gauge for pneumatic balls, comprising:

a rigid clamp arm;

a flexible clamp arm pivotally connected to said rigid clamp arm at a mutual fulcrum;

a socket in said rigid clamp arm facing said flexible clamp arm for holding a ball to be tested;

the two clamp arms capable of partially compressing the ball between them in said socket;

means for releasably latching the two clamp arms together in a clamped position on the ball; and, means for indicating the amount of distortion in said flexible clamp arm caused by the partial compression of the ball;

whereby an indication of gas pressure in the ball is obtained by placing the ball in said socket between the two clamp arms, latching the two clamp arms together, and reading the indicated amount of flex in said flexible clamp arm.

10. A pressure gauge for pneumatic balls, comprising:

a rigid clamp arm;

a flexible clamp arm pivotally connected to said rigid clamp arm at a mutual fulcrum;

a socket in said rigid clamp arm facing said flexible clamp arm for holding a ball to be tested;

a probe on said flexible clamp arm extending partly into said socket to partially compress the ball therein when the two clamp arms are rotated toward each other in a clamping action;

a pointer arm having first and second ends, the first end journalled to said mutual fulcrum;

and, adjustment means for attaching the first end of said pointer arm to said flexible clamp arm at an adjustable angle between said pointer arm and said flexible clamp arm;

whereby an indication of gas pressure in a ball is obtained by placing the ball in said socket between the two clamp arms, clamping the two clamp arms together, and observing the amount of flex in said flexible clamp arm as indicated by the position of said pointer arm.

* * * * *